United States Patent
You

(10) Patent No.: US 10,149,888 B2
(45) Date of Patent: Dec. 11, 2018

(54) METHOD OF INHIBITING HIV REPLICATION UTILIZING THE P7 NUCLEOCAPSID PROTEIN

(75) Inventor: Ji Chang You, Seoul (KR)

(73) Assignees: Ji Chang You, Seoul (KR); AVIXGEN INC., Seoul (KR)

( * ) Notice: Subject to any disclaimer, the term of this patent is extended or adjusted under 35 U.S.C. 154(b) by 0 days.

(21) Appl. No.: 12/527,235

(22) PCT Filed: Feb. 13, 2008

(86) PCT No.: PCT/KR2008/000827
§ 371 (c)(1),
(2), (4) Date: Aug. 14, 2009

(87) PCT Pub. No.: WO2008/100061
PCT Pub. Date: Aug. 21, 2008

(65) Prior Publication Data
US 2010/0075901 A1 Mar. 25, 2010

(30) Foreign Application Priority Data
Feb. 16, 2007 (KR) .................. 10-2007-0016786

(51) Int. Cl.
*A61K 38/16* (2006.01)
*G01N 33/569* (2006.01)

(52) U.S. Cl.
CPC ..... *A61K 38/162* (2013.01); *G01N 33/56988* (2013.01); *C12N 2740/16222* (2013.01); *C12N 2740/16322* (2013.01)

(58) Field of Classification Search
CPC ................... A61K 38/162; C12N 2740/16222
See application file for complete search history.

(56) References Cited

U.S. PATENT DOCUMENTS

| 5,576,421 | A  | * | 11/1996 | Saito et al. .................. 530/350 |
| 6,733,993 | B2 | * | 5/2004  | Emini et al. ................. 435/69.1 |
| 6,841,535 | B2 | * | 1/2005  | Divita et al. ............... 424/130.1 |
| 6,958,226 | B1 | * | 10/2005 | Gray et al. .................. 435/91.4 |

OTHER PUBLICATIONS

Cen, S., et al., 1999, The role of Pr55gag in the annealing of tRNA3Lys to human immunodeficiency virus type 1 genomic RNA, J. Virol. 73(5):4485-4488.*
Invitrogen, Apr. 2006, Map and Features of pLP1, in ViraPower Lentiviral Expression Systems manual, pp. 1-2.*
Luukkonen, B. G. M., and S. Schwartz, 1998, Reduced infectivity of human immunodeficiency virus type 1 produced in the presence of a truncated Gag protein containing p7 gag and p6 gag, Arch. Virol. 143:1395-1403.*
ViraPower Lentiviral Expression Systems: Lentiviral systems for high-level expression in dividing and non-dividing mammalian cells, 2006, Invitrogen User Manual, pp. 30-31.*
Schüpbach,"Viral RNA and p24 antigen as markers of HIV disease and antiretroviral treatment success", Int Arch Allergy Immunol, 2003, vol. 132, pp. 196-209.
Parpia et al., "p24 Antigen Rapid Test for Diagnosis of Acute Pediatric HIV Infection", J Acquir Immune Defic Syndr, 2010, vol. 55, No. 4, pp. 413-419.

* cited by examiner

*Primary Examiner* — Jeffrey S Parkin
(74) *Attorney, Agent, or Firm* — Lucas & Mercanti, LLP

(57) ABSTRACT

The present invention relates to a novel use of the HIV NC protein, and more particularly, it is relates to a pharmaceutical composition for preventing and treating AIDS having a polypeptide comprising HIV NC protein as an active component and the method of inhibiting HIV proliferation by using the polypeptide. The polypeptide comprising HIV NC protein of the present invention, when it is overexpressed, has the effect on inhibiting HIV proliferation. Accordingly, the present invention provides not only the novel means of inhibition of HIV proliferation, but also the novel method for preventing and treating AIDS.

4 Claims, 5 Drawing Sheets

Specification includes a Sequence Listing.

METHOD OF INHIBITING HIV REPLICATION UTILIZING THE P7 NUCLEOCAPSID PROTEIN

CROSS-REFERENCES TO RELATED APPLICATIONS

This application is a U.S. national phase application, pursuant to 35 U.S.C. § 371, of PCT/KR2008/000827, filed Feb. 13, 2008, designating the United States, which claims priority to Korean Application No. 10-2007-0016786, filed Feb. 16, 2007. The entire contents of the aforementioned patent applications are incorporated herein by this reference.

TECHNICAL FIELD

The present invention relates to a novel use of HIV NC protein, and more particularly to a pharmaceutical composition for preventing and treating AIDS having a polypeptide comprising HIV NC protein, as effective components, to the method for preventing and treating AIDS comprising administration to subject in need thereof an effective amount, to a novel use of HIV NC protein for preparing agents for preventing and treating AIDS, and to method of inhibiting HIV proliferation by using the said polypeptide.

BACKGROUND ART

AIDS (Acquired Immune Deficiency Syndrome), identified for the first time in the early 1980s, is one of the most important diseases in the world. AIDS-treating drugs, developed to date, include protease inhibitors, such as saquinavir, indinavir and ritonavir, and reverse transcriptase inhibitors, such as AZT, ddI, ddC, d4T, 3TC and nevirapine. It is known that when such treating drugs are used alone, they have no significant effect, but when two reverse transcriptase inhibitors, such as AZT and 3TC, and one protease inhibitor, are used in combination, they show a high therapeutic effect.

However, the drug combinations do not improve disease conditions in all patients who were administered them, and moreover they have problems in that they are expensive and have serious side effects, including vomiting and high fever, and appearance of variant viruses having tolerance to these drugs appear.

Accordingly, for better therapy, there is a need to develop a novel class of therapeutic agents, which are more effective and have low toxicity.

AIDS is caused by infection with HIV (human immunodeficiency virus), and at 3-6 weeks after infection, the person suffers from symptoms such as cold and fatigue, for about 1-2 weeks, and then recovered from the symptoms. Thereafter, the long latent period of HIV is lasting for about 10 years. During the long latent period, HIV virus destroys the immune cells of the infected person while it continues to proliferate. Thus, the immune function of the patient is gradually impaired, so that AIDS symptoms appear at the last stage of the latent period.

Among HIV proteins, an nucleocapsid protein (hereinbelow, referred to as 'NC') performs not only a structural function of forming virus individuals, but also an important function in the viral life cycle. The major functions of the HIV NC protein are as follows. First, the NC protein is involved in viral genomic encapsidation. This function is attributable to two zinc finger domains consisting of a unique Cys-X2-Cys-X4-His-X4-Cys motif (CCHC motif), and it is known that the domains are highly conserved in all retroviruses and are essential for HIV RNA packaging and infectious virus production. Second, the NC protein is known to promote tRNA primer annealing and strand transfer during viral reverse transcription (RT), and this suggests that the NC protein plays an important role in viral replication. Third, the NC protein has nucleic acid chaperone activity necessary for the viral life cycle, and recently, it was reported that, even when the viral DNA is inserted into the host cell chromosome, the NC protein plays a certain role.

Accordingly, the studies about the NC protein are very important in the view of developing antiviral agent against the essential HIV proteins as well as disclosing biological function of the NC protein during the HIV life cycle.

DISCLOSURE OF INVENTION

Technical Problem

Accordingly, the present inventors have conducted studies on the physiological activity of the HIV NC protein, and as a result, have found that the HIV NC protein and the polypeptide comprising the HIV NC protein shows an activity of inhibiting the proliferation of the HIV. On the basis of this finding, the present inventors have developed a novel use of the said polypeptide for preventing and treating AIDS, thereby completing the present invention.

Therefore, it is an object of the present invention to provide a novel use of HIV NC protein.

Technical Solution

To achieve the above object, in one aspect, the present invention provides a pharmaceutical composition for preventing and treating AIDS comprising a polypeptide comprising HIV NC protein as an active component.

In another aspect, the present invention provides a method for inhibiting HIV proliferation by increasing the intracellular level of a polypeptide comprising HIV NC protein.

In still another aspect, the present invention provides a screening method of agents for preventing or treating AIDS comprising identifying the candidate substance increasing the intracellular level of the polypeptide comprising HIV NC protein.

Hereinafter, the present invention will be described in detail.

The inventive composition comprises HIV (human immunodeficiency virus) NC (Nucleocapsid) itself or a polypeptide which contains HIV NC protein as an effective component. As used herein, "HIV NC protein" means the nucleocapsid protein of HIV (Human Immunodeficiency Virus) causing AIDS (Acquired Immune Deficiency Syndrome. This protein strongly binds to virus genomic RNA to form a ribonucleoprotein core complex.

Preferably, the HIV NC protein may have an amino acid sequence represented by SEQ ID NO: 1 and may be the NC protein set forth in Genbank Accession Nos. P03349, P03366, P04585, P03367, P12497, P03369, P04587, P04584, P35963, P24740, P05961, P04591, Q73368, P20892, P20875, P12498, P05888, P12493, Q9QBZ5, Q9QBY3, O89940, Q9WC63, Q9WC54, Q75002, P24736, Q9QBZ1, O89290, Q9QBZ6, Q9QBY4, P12499, P05959, P18802, P04588, P04589, P05960, Q70622, P20889, P12494, P03347, Q9QSR3, Q9Q720, Q9IDV9, Q9WC62, Q9WC53, Q9Q721, Q74230, Q73367, O12157, P35962, P18800, P04592, P20873, P05887, P03348, P04593, Q89928, Q79666, Q77373, O41798, O93215, O91080, P05962, Q9QBZ2, Q9QC00, O89291, P05891, P15833, P17757, P18096, Q9QSR4, Q9IDV8, Q75001, O89939, P18095, P05890, P04594, P12495, Q76634, P20876, P18042, P0C1K7, Q79665, Q77372, O93182, O91079, P05889, P12451, P24107, Q76633, P12450, P18041, P15832, P24106, P17756, Q69383, Q74120, Q74119, P20874, P04590, P03363, Q0R5R2, Q1A268, Q1A250, Q1A267, P03353, Q0R5R3 and Q1A249. For example, in the case of P03349, the NC protein may be a sequence consisting of amino acid residues 380 to 434.

In addition, a polypeptide which contains HIV NC protein of the present invention, may be, but are not limited to, gag deleted mutant of HIV. Preferably, it may be amino acid SEQ ID NOs: 2 to 7.

HIV NC protein in the present invention, could inhibit HIV proliferation effectively, when it is expressed within the cell (Example 1), and gag deleted mutant comprising HIV NC protein also inhibited HIV proliferation effectively (Example 2). These facts were disclosed for the first time by the present inventors. Accordingly, the present invention provides a pharmaceutical composition for preventing and treating AIDS having a polypeptide comprising HIV NC protein as an active component.

The inventive pharmaceutical composition may comprise a pharmaceutically effective amount of HIV NC protein itself or a polypeptide, which contains HIV NC protein alone or with one or more pharmaceutically acceptable carriers. The said "pharmaceutically effective amount" means the amount which has the same or more effect compared with a control group, and preferably, enough amount for preventing and treating AIDS.

The effective amount of the HIV NC protein or a polypeptide containing HIV NC protein is about 0.0001 to 100 mg/day/kg body weight, more preferably 0.01 to 1 mg/day/kg body weight. However, it may be suitably determined by considering various factors, such as age, body weight, health condition, sex, disease severity, diet and excretion of a subject in need of treatment, as well as administration time and administration route.

As used herein, the term "pharmaceutically acceptable" means what is physiologically acceptable and, when administered to human beings, generally does not cause allergic reactions, such as gastrointestinal disorder and dizziness, or similar reactions thereto. The carrier or excipient can include, but not limited to, all kinds of solvents, dispersing agents, water-in-oil (W/O) or oil-in-water (O/W) emulsion, aqueous compounds, liposome, microbead or microsome.

Also, the inventive pharmaceutical composition may be formulated with proper carriers according to administering routes. The inventive pharmaceutical composition may be administered, but not limited to, by oral or parenteral routes. For example, the parenteral routes include methods for applying to transdermal, intranasal, intraperitoneal, intramuscular, subcutaneous or intravenous.

For oral administration, the inventive pharmaceutical composition could be formulated, as known in the art, in the form of powder, granule, tablet, buccal tablets, sugarcoated tablet, capsules, elixirs, gel, syrups, suspensions, wafers, and the like. These preparations may also comprise acceptable carriers such as polysaccharides including lactose, dextrose, sucrose, sorbitol, mannitol, xylitol, erythritol, and maltitol, starches including corn starch, wheat starch, rice starch, and potato starch, celluloses including cellulose, methylcellulose, sodium carboxymethylcellulose and hydroxypropylmethyl cellulose, and fillers such as gelatin and polyvinylpyrrolidone. In addition, in some cases, these preparations may also comprise disintegrating agents such as cross-linked polyvinylpyrrolidone, agar, alginic acid or sodium alginates. Moreover, the inventive the pharmaceutical composition may further comprise anti-agglutinant, lubricant, wetting agent, flavors, emulsifier, preservative and so on.

In case of parenteral administration, the inventive pharmaceutical composition could be formulated, as known in the art, in the form of injectable formulation, transdermal formulation and intranasal formulation with proper parenteral carriers. The injectable formulation must be sterilized and prevented from contamination of microorganisms such as fungi and bacteria. In case of injectable formulation, the carriers may comprise, but not limited to, water, ethanol, polyol (for example, glycerol, propylene glycol, liquid polyethylene glycol and the like), mixture of these and/or solvent including vegetable oils or dispersion medium. More preferably, the carriers may comprise Hank's solution, Ringer's solution, PBS (phosphate buffered saline) containing triethanolamine, or isotonic solutions such as water for injection, 10% ethanol, 40% propylene glycol, 5% dextrose. To prevent from contamination of microorganisms, the injectable agents may comprise additionally anti-fungal reagents and anti-bacterial reagents such as parabens, chlorobutanol, phenol, sorbic acid, thimerosal. The injectable formulation may also comprise isotonic solution such as saccharides or sodium chloride.

The transdermal formulation may include ointment, cream, lotion, gel, external liquid, paste, liniment, aerosol. The transdermal administration means that the pharmaceutical composition is locally administered such that an effective amount of an active ingredient contained in the pharmaceutical composition is transferred into the skin. These formulations are described in *Remington's Pharmaceutical Science*, 15th Edition, 1975, Mack Publishing Company, Easton, Pa.

In case of intranasal preparations, the inventive pharmaceutical composition may comprise proper propellant such as dichlorofluoromethane, trichlorofluoromethane, dichlorotertafluoroethane, carbon dioxide, and the like. By these propellants, the composition could be released easily from pressurized pack or spray container in the form aerosol spray. In case of the pressurized aerosol, administration dosage may be set by placing a valve. For example, gelatin capsules and cartridges which are used in inhalers and insufflators may comprise a proper powder mixture such as a chemical compound, lactose, or starches Another carriers which is pharmaceutically acceptable is disclosed in Remington's Pharmaceutical Sciences, 19th ed. Mack Publishing Company, Easton, Pa., 1995, the entire disclosure of which is incorporated herein by reference.

The inventive pharmaceutical composition may further comprise one or more buffers (for example, saline or PBS), carbohydrates (for example, glucose, mannose, sucrose, or dextran), antioxidants, bacteriostats, chelating reagents (for example, EDTA or glutathione), adjuvant (for example, aluminium hydroxide), suspension reagent, concentrating reagent, and/or preservatives.

Also, the inventive pharmaceutical composition may be formulated by using the method which is known in the art, to provide rapid, continuous or delayed release after administered to a mammalian.

Also, the inventive pharmaceutical composition may be administered together with well-known compounds which have effects in preventing or treating AIDS.

Meanwhile, the present invention provides a pharmaceutical composition for preventing and treating AIDS (acquired immune deficiency syndrome) comprising an expression vector which comprise a promoter and a polynucleotide encoding a polypeptide comprising an HIV NC (human immunodeficiency virus nucleocapsid) protein operably linked to the promoter as an effective component. And the polynucleotide may have the nucleotide sequence selected from the group consisting of SEQ ID NO: 8 to 14, and preferably the expression vector may be pLP1/optiNC vector.

Meanwhile, the present invention provides a method for inhibiting HIV proliferation by increasing the intracellular level of a polypeptide comprising HIV NC protein.

The intracellular level means the amount existing in the cells, and it may be regulated via various method which is known in the art. For example, but not limited thereto, the intracellular level may be regulated through transcription steps. The regulation through transcription steps may performed by the known method for increasing expression of gene, for example, a transformation method of cell with an expression vector which comprises a promoter and a polynucleotide encoding HIV NC protein itself or a polypeptide comprising HIV NC protein, for example, the polynucleotide having a nucleotide sequence of SEQ ID NO: 8 to 14. As another example of increasing intracellular level, it may be performed by a transfer method of a polypeptide comprising HIV NC protein to a target cell. These transfer method may be performed according to suitable method which is modified by a conventional gene therapy method to purpose of the present invention and these are published well to known in the art.

As the promoter, a constitutive promoter that constitutively induces the expression of a target protein can be used, and examples thereof include a CaMV 35S promoter (Odell et al., *Nature* 313:810-812, 1985), an Rsyn7 promoter (U.S. patent application Ser. No. 08/991,601), a rice actin promoter (McElroy et al., *Plant Cell* 2:163-171, 1990), an uiquitin promoter (Christensen et al., *Plant Mol. Biol.* 12:619-632, 1989), an ALS promoter (U.S. patent application Ser. No. 08/409,297), etc. Also usable promoters are disclosed in U.S. Pat. Nos. 5,608,149, 5,608,144, 5,604,121, 5,569,597, 5,466,785, 5,399,680, 5,268,463, 5,608,142, etc.

The "promoter" means a DNA sequence regulating the expression of nucleic acid sequence operably linked to the promoter in a specific host cell, and the term "operably linked" means that one nucleic acid fragment is linked to other nucleic acid fragment so that the function or expression thereof is affected by the other nucleic acid fragment. Additionally, the promoter may include a operator sequence for controlling transcription, a sequence encoding a suitable mRNA ribosome-binding site, and sequences controlling the termination transcription and translation. Additionally, it may be constitutive promoter which constitutively induces the expression of a target gene, or inducible promoter which induces the expression of a target gene at a specific site and a specific time, and examples thereof include a SV40 promoter, CMV promoter, CAG promoter (Hitoshi Niwa et al., *Gene,* 108:193-199, 1991; Monahan et al., *Gene Therapy,* 7:24-30, 2000), CaMV 35S promoter (Odell et al., Nature 313:810-812, 1985), Rsyn7 promoter (U.S. patent application Ser. No. 08/991,601), rice actin promoter (McElroy et al., *Plant Cell* 2:163-171, 1990), Ubiquitin promoter (Christensen et al., *Plant Mol. Biol.* 12:619-632, 1989), ALS promoter (U.S. patent application Ser. No. 08/409,297). Also usable promoters are disclosed in U.S. Pat. Nos. 5,608,149; 5,608,144; 5,604,121; 5,569,597; 5,466,785; 5,399,680; 5,268,463; and 5,608,142, etc.)

Examples of the vector of the present invention include a plasmid vector, a cosmid vector, a bacteriophage vector and a viral vector, but are not limited thereto. The preferred expression vector includes regulatory elements for gene expression such as a promoter, operator, an initiation codon, a stop codon, a polyadenylation signal, and an enhancer, and a variety of vectors can be prepared according to the purpose. The vector of the present invention may be preferably a pLP1/optiNC vector.

The pLP1/optiNC vector was prepared in the following manner. A codon-optimized HIV NC gene (OptiNC DNA) of SEQ ID NO: 15 was digested with restriction enzymes EcoRI and HindIII, and the digested fragment was cloned into a pUC57 vector (Genescript, USA), digested with the restriction enzymes EcoRI and HindIII. The resulting vector was named "pUC57/OptiNC". The pUC57/OptiNC and pcDNA4/TO (Invitrogen, USA) were digested with HindIII and EcoRI, and then ligated to each other, thus constructing pcDNA4/TO/OpicNC. The pcDNA4/TO/OptiNC was digested with HindIII and NotI, and then the digested, HIV NCgene-containing DNA fragment was polymerized with the Klenow fragment, thus obtaining a blunt-end fragment. Also, the pCMV(-HA) vector (Clontech Laboratories, Inc., USA) was digested with EcoRI and NotI, and then the digested DNA fragment was polymerized with the Klenow fragment, thus obtaining a blunt-end fragment. The two fragments, obtained by treatment with the Klenow fragment, were ligated to each other, and the resulting vector was named "pCMV(-HA)/OptiNC". The pLP1 vector (Invitrogen) was digested with Pm/I/AvrII/BspEI to remove the GAG-POL gene, and the OptiNC polynucleotide was digested with XmaI/EcoRI and ligated into the pCMV(-HA)/OptiNC vector. The pLP1 vector and the OptiNC polynucleotide were all polymerized with the Klenow fragment to obtain blunt-end fragments, which were then subjected to blunt end ligation. The resulting vector was named "pLP1/optiNC".

Meanwhile, standard recombinant DNA and molecular cloning techniques which are used in the present invention are well known in the art, and described well in the following references. (Sambrook, J., Fritsch, E. F. and Maniatis, T., Molecular Cloning: A Laboratory Manual, 2nd ed., Cold Spring Harbor Laboratory: Cold Spring Harbor, N.Y. (1989); by Silhavy, T. J., Bennan, M. L. and Enquist, L. W., Experiments with Gene Fusions, Cold Spring Harbor Laboratory: Cold Spring Harbor, N.Y. (1984); and by Ausubel, F. M. et al., Current Protocols in Molecular Biology, published by Greene Publishing Assoc. and Wiley-Interscience (1987)).

As described above, the expression of the HIV NC protein and the polypeptide comprising HIV NC protein shows an activity of inhibiting the proliferation of HIV. Accordingly, the present invention provides a screening method of agents for preventing or treating AIDS, the method comprising investigating a substance which increases the expression of the HIV NC protein and the polypeptide comprising HIV NC protein.

Specifically, the screening method of agents for preventing or treating AIDS comprising the steps of:

(a) culturing recombinant cells expressing the polypeptide comprising HIV NC protein with a candidate substance; and (b) measuring the effect of the candidate substance on increasing the intracellular level of the polypeptide comprising HIV NC protein.

As used herein, the term "increasing the intracellular level of the polypeptide comprising HIV NC protein" means that the concentration of the polypeptide in the cells is increased through the increase of the expression of a gene encoding the polypeptide. Thus, the candidate substances in the present invention are those having characteristics of promoting the expression of the polypeptide. The anticancer substances include not only proteins, but also compounds or extracts, isolated in nature or chemically synthesized.

The measurement of the intracellular level of the polypeptide comprising HIV NC protein can be carried out using various methods known in the art. Examples of the method of measuring the intracellular level of the polypeptide include, but are not limited to, co-immunoprecipitation, enzyme-linked immunosorbent assay, radioimmunoassay (RIA), immunohistochemical assay, Western blotting, and fluorescence activated cell sorting (FACS).

Also, the inventive screening method targeting the polypeptide can be performed using high throughput screening (HTS). The HTS is a method for screening the biological activities of multiple candidate substances simultaneously or almost simultaneously by testing the multiple candidate substances at the same time. In a certain embodiment, a cell line is cultured in a 96-well microtiter plate or a 192-well microtiter plate and treated with multiple candidate substances, and then the expression of the polypeptide comprising HIV NC protein is measured using an immunohistochemical method. In this format, 96 independent tests may be simultaneously performed in a single 8 cm×12 cm plastic plate containing 96 reaction wells. The wells require an assay volume of typically 50-500 □. In addition to the plate, a number of gauges, instruments, pipetters, robots, plate washers and plate readers are commercially available in order to make the 96-well format suitable for a wide range of homogeneous and heterogeneous assays.

In one Example of the present invention, 293FT cells were transformed by introducing therein the vector pNL4-3GFP capable of producing HIV viruses and the pLP1/optiNC vector expressing the HIV NC protein, and the number of HIV viruses proliferated in the transformed 293FT cells was analyzed. As a result, it could be seen that the inhibition of proliferation of HIV in the cells expressing the HIV NC protein was about 100-fold higher than in the cells not expressing the HIV NC protein (see Example 1 and FIG. 1).

In another Example of the present invention, six kinds of vectors expressing HIV NC protein-containing Gag deletion mutants were prepared, and the prepared vectors were transformed into 293FT cells together with the pNL4-3GFP vector. Then, the number of HIV viruses proliferated in the transformed 293FT cells was analyzed. As a result, the inhibition of proliferation of HIV in the cells expressing the deletion mutant was about 5-70-fold higher than in the cells not expressing the deletion mutant (see Example 2 and FIG. 5).

Based on the effect of the HIV NC protein of the present invention, the present inventor provides a method for preventing or treating AIDS comprising administering to subject in need thereof an effective amount of HIV NC protein.

As used herein, the term "effective amount" refers to an amount effective in preventing or treating AIDS in the subject to be administered, and the subject may comprise mammals, especially animals including human. The subject may be patients in need of treatment.

The HIV protein of the present invention may be administered until desirable effect was induced, and may be administered via various routes. That is, via oral or parenteral routes, for example, oral, intramuscular, intravenous, intracutaneous, intraarterial, intramarrow, intrathecal, intraperitoneal, intranasal, intravaginal, intrarectal, sublingual and subcutaneous or administering to gastrointestinal tracts, mucosa or respiratory organs systemically.

Also, this invention provides an use of HIV NC protein for manufacturing agents for treating AIDS. AIDS, HIV protein of the present invention and its effect are described well in the above.

Moreover, the present invention provides the method for preventing and treating AIDS comprising administration to subject in need thereof an effective amount of an expression vector which comprise a promoter and a polynucleotide encoding a polypeptide comprising an HIV NC (human immunodeficiency virus nucleocapsid) protein operably linked to the promoter.

The present invention also provides an use of an expression vector, which comprise a promoter and a polynucleotide encoding a polypeptide comprising an HIV NC (human immunodeficiency virus nucleocapsid) protein operably linked to the promoter for manufacturing agents for treating AIDS. The polynucleotide, the expression vector, subject, effective amount, and AIDS are described well in the above.

Advantageous Effects

Accordingly, the polypeptide comprising HIV NC protein of the present invention, when is overexpressed, has the effect on inhibiting HIV proliferation. Accordingly, the present invention provides not only the means of inhibition of HIV proliferation, but also the novel method for preventing and treating AIDS.

BEST MODE FOR CARRYING OUT THE INVENTION

Figure 1:
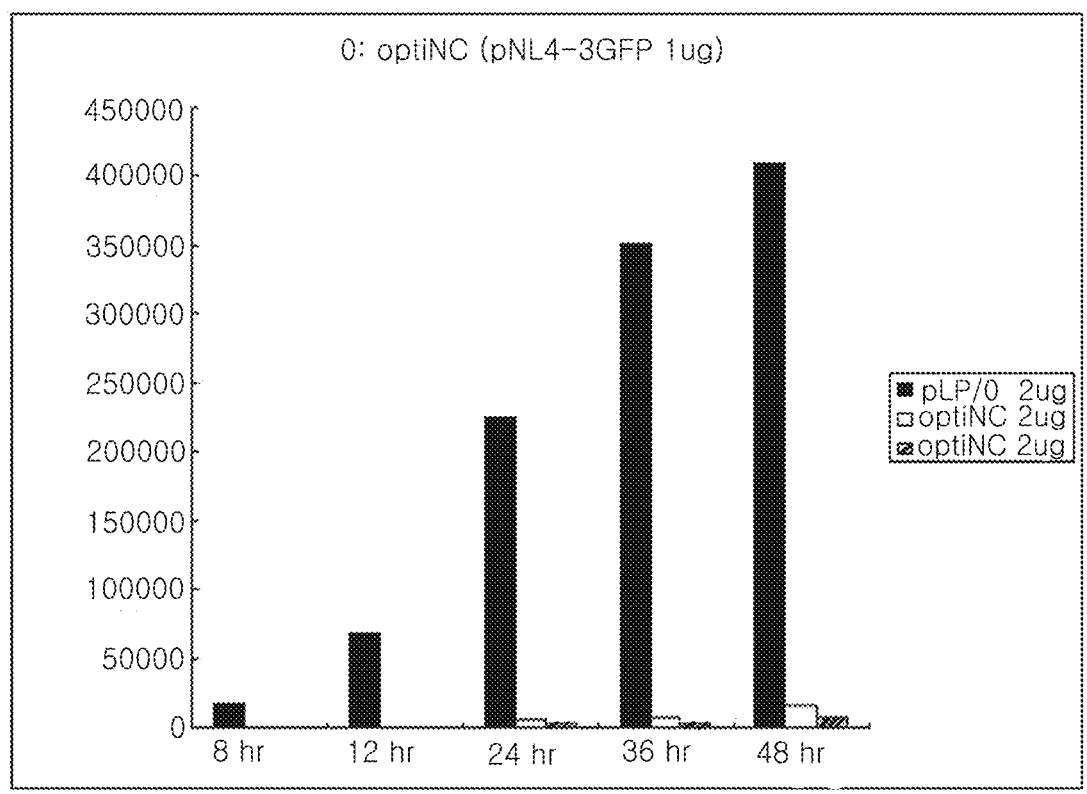
FIG. 1 shows the effect of HIV NC protein in inhibiting proliferation of HIV.

Hereinafter, the present invention will be described in further detail with reference to examples. It is to be understood, however, that these examples are illustrative only, and the scope of the present invention is not limited thereto.

Example 1: Examination of Effect of NC Protein on Inhibition of HIV Proliferation <1-1> Construction of Transformed Cells Expressing NC Protein 293FT cells (Invitrogen, USA), used in transformation, were cultured in a DMEM (Dulbecco's modified Eagle medium), containing 10% fetal bovine serum, 1% penicillin/streptomycin and 1% nonessential amino acid, in conditions of 37° C. and 5% $CO_2$. After the 293FT cells were cultured in a 6-well plate for 24 hours, the cells were transformed with the pNL4-3GFP vector and the pLP1/optiNC vector according to the lipofectamine 2000 protocol (invitrogen, USA). As a control group producing no NC protein, a pLP1/0 vector (that is, nothing was inserted into the pLP1 vector) was used instead of the pLP1/optiNC vector. The transformation was carried out in the following manner. The cells were cultured in a 6-well plate to a confluence of about 90%. Each of a mixture of 1 µg of the pNL4-3GFP vector and 2 µg of the pLP1/optiNC vector, a mixture of 1 µg of pNL4-3GFP and 3 µg of the pLP1/optiNC vector, and a mixture of 1 µg of the pNL4-3GFP vector and 2 µg of pLP1/0, as a control group, was prepared, and then diluted in 250 µl of opti-MEM I reduced serum medium. Meanwhile, 9 µl of the lipofectamine 2000 was diluted in 250 µl of opti-MEM medium, and then left to stand at room temperature for 5 minutes. Thereafter, the diluted lipofectamine 2000 was added to each of the vector mixtures, and then left to stand for about 30 minutes. The cells, cultured in the 6-well plate, were washed with 500 µl of PBS (phosphate-buffered saline), and then added to 500 µl of opti-MEM medium. The mixture of each of the vector mixtures with the lipofectamine 2000 was added to each of the culture media and cultured in conditions of 37° C. and 5% $CO_2$.

The vectors, used in the transformation of the cells, will now be described in detail. The pNL4-3EGFP vector is a vector capable of producing recombinant HIV virus, because it contains all HIV-1 genes, except that half of the Nef gene is replaced with the EGFP reporter gene. This vector is described in detail in the published literature (Lee et al., 1997, Biochem. Biophy. Res. Comm., 233: 288-292). The pLP1/optiNC vector is a vector for expressing the NC protein, and the pLP1/0 vector in which the fragment corresponding to the NC gene in the pLP1/optiNC vector is not inserted.

<1-2> Measurement of Rate of HIV Proliferation according to Expression of NC

The media of the 293FT cells, transformed in Example <1-1>, were replaced with sodium pyruvate-containing DMEM media at 5-6 hours after the transformation of the cells. Then, at 6 hours, 12 hours, 24 hours, 36 hours and 48 hours, samples were collected from the media, and the contents of the virus in the samples were measured by ELISA analysis.

The ELISA analysis was carried out using a Vironostika HIV-1 antigen p24 ELISA kit (Biomerieux, France) according to the manufacturer's instruction. Specifically, each of the medium samples was transferred to and incubated in the well of the kit and washed four times by mixing each sample with 100 µl of phosphate buffer (0.17 M $KH_2PO_4$, 0.72 M $K_2HPO_4$) and allowing the mixture to stand for 30 seconds. Then, each of the medium samples was allowed to react with a p24 antibody at 37° C. for 1 hour, and then with a HRP (horseradish peroxidase)-conjugated secondary antibody at 37° C. for 1 hour. Tetramethylbenzidine (TMB) was added thereto and conjugated with the antibody complex for 10 minutes. Then, the samples were serially diluted two-fold from 80 pg/ml to 5 pg/ml and were measured for their absorbance at 450 nm to determine the amount of the virus in each of the samples.

As a result, as can be seen in FIG. 1 and Table 1 (unit: pg/ml) below, the NC protein concentration-dependently inhibited the production of the HIV virus. Particularly, the inhibition of proliferation of the HIV virus in the cells, to which 3 µg of the NC protein-expressing vector (pLP1/optiNC vector) was added at 48 hours after the transformation of the cells, was about 100-fold higher than in the cells not expressing the NC protein. This result suggests that the NC protein can be used as an antiviral agent for inhibiting the proliferation of the HIV virus.

TABLE 1

|  | 8 hr | 12 hr | 24 hr | 36 hr | 48 hr |
|---|---|---|---|---|---|
| pNL4-3EGFP(1 µg) + pLP1/0(2 µg) | 17615.14 | 67442.3 | 226266.4 | 350834.2 | 410004 |
| pNL4-3EGFP(1 µg) + pLP1/optiNC(2 µg) | 111.535 | 181.964 | 5566.944 | 7985.42 | 15466.862 |
| pNL4-3EGFP(1 µg) + pLP1/optiNC(3 µg) | 45.04886 | 50.409 | 2125.266 | 2719.573 | 7825.96 |

<2-1> Preparation of Gag Deletion Mutant

Figure 2:
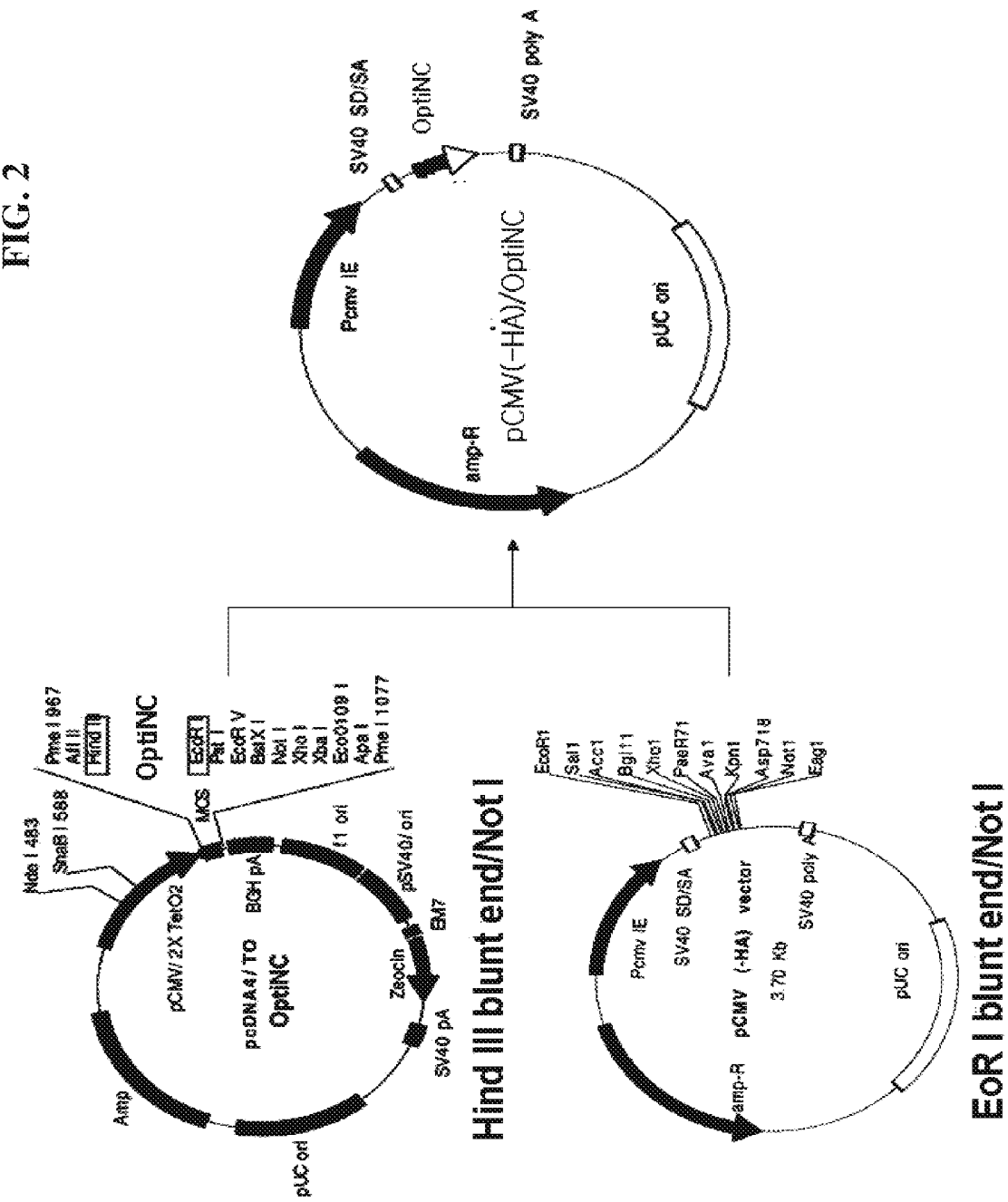
FIGS. 2 and 3 schematically show a process of preparing pLP1/optiNC expression vector of the present invention.
Figure 3:
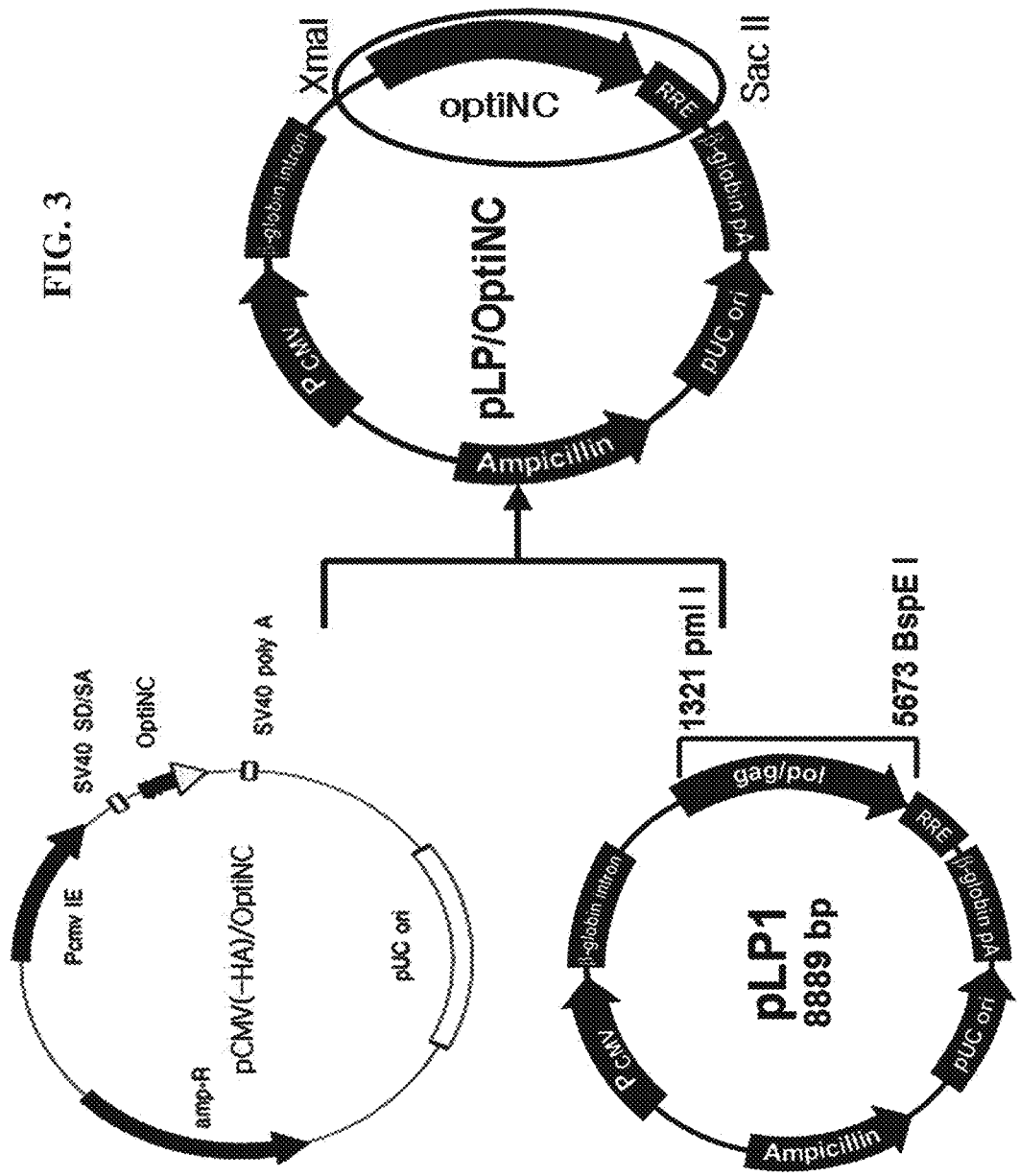
Figure 4:
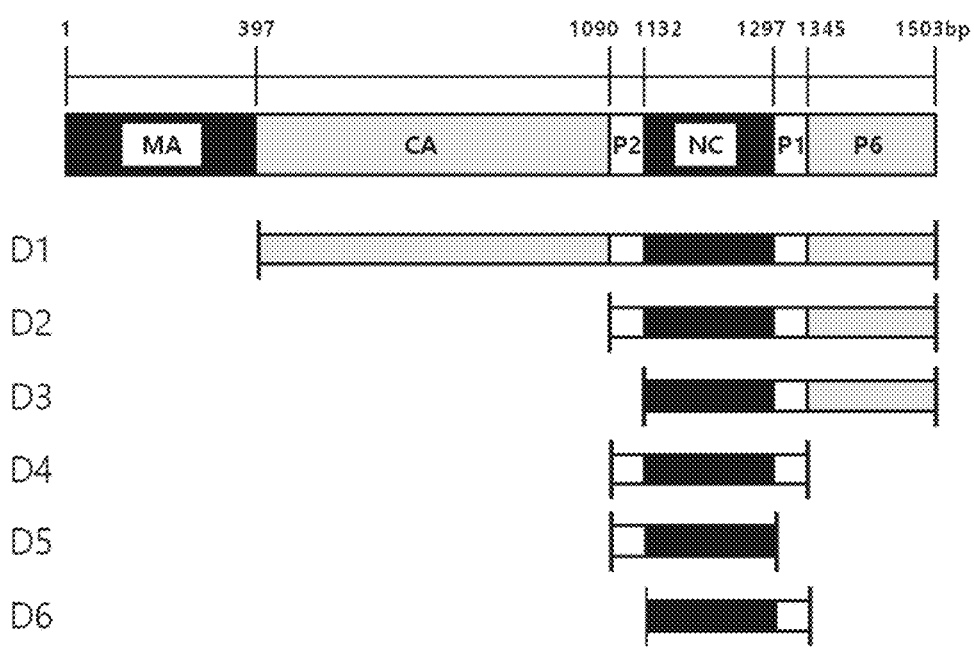
FIG. 4 schematically shows 6 gag deleted mutants which contain HIV NC protein, respectively. The abbreviation for HIV gag protein domain means as follows. MA (Matrix), CA (Capsid), P2 (P2 domain), NC (Nucleocapsid), P1 (P1 domain), P6 (P6 domain).

In order to the effect of NC protein-containing Gag deletion mutants on the inhibition of proliferation of the HIV virus, 6 kinds of Gag deletion mutants were prepared. Using the sequence information of pLP1, the PCR primers shown in Table 2 below were designed in order to prepare NC protein-containing Gag deletion mutants as shown in FIG. 2.

TABLE 2

| Deletion mutants | Forward primers | Reverse Primers |
|---|---|---|
| D1 | tttctagaggacacgtgatggtgcagaacatc (SEQ ID NO: 16) | ccctcgagtccggattattgtgacga (SEQ ID NO: 19) |
| D2 | tttctagaggacacgtgatggctgaagcaatg (SEQ ID NO: 17) | ccctcgagtccggattattgtgacga (SEQ ID NO: 19) |
| D3 | tttgtagaggacacgtgatgatacagaaa (SEQ ID NO: 18) | ccctcgagtccggattattgtgacga (SEQ ID NO: 19) |
| D4 | tttctagaggacacgtgatggctgaagcaatg (SEQ ID NO: 17) | ccctcgagtccggatcaaaaattccctgg (SEQ ID NO: 20) |

TABLE 2-continued

| Deletion mutants | Forward primers | Reverse Primers |
|---|---|---|
| D5 | tttctagaggacacgtgatggctgaagcaatg (SEQ ID NO: 17) | ccctcgagtccggatcaattagcctgtct (SEQ ID NO: 21) |
| D6 | tttgtagaggacacgtgatgatacagaaa SEQ ID NO: 18) | ccctcgagtccggatcaaaaattccctgg (SEQ ID NO: 20) |

The six kinds of deletion mutants were amplified by PCR in the following conditions using each primer combination shown in Table 2 and the pLP1 vector as a template: predenaturation at 95° C. for 5 min, and then 25 cycles of 30 sec at 95° C., 30 sec at 58° C. and 30 sec at 72° C., followed by extension at 72° C. for 5 min. Each of the amplified PCR products was digested with pmlI and BspEI and cloned into the pmlI and BspEI restriction enzyme sites of the pLP1 vector. The resulting vectors were named "pLP1-D1" to "pLP1-D6".

Example 2: Analysis of Effects of NC Protein-Containing Gag Deletion Mutants on Inhibition of HIV Proliferation <2-2> Measurement of Rate of HIV Proliferation According to Expression of NC Protein In order to measure the effect of the expression of each Gag deletion mutant, prepared in Example <2-1>, on the rate of HIV proliferation, the measurement method of Examples <1-1> and Example <1-2> was repeated, except that 1 μg of each of said pLP1-D1 to pLP1-D6 vectors expressing the mutants was used instead of the pLP1/optiNC vector and that the medium samples were collected 24 hours after replacement with DMEM media.

Figure 5:
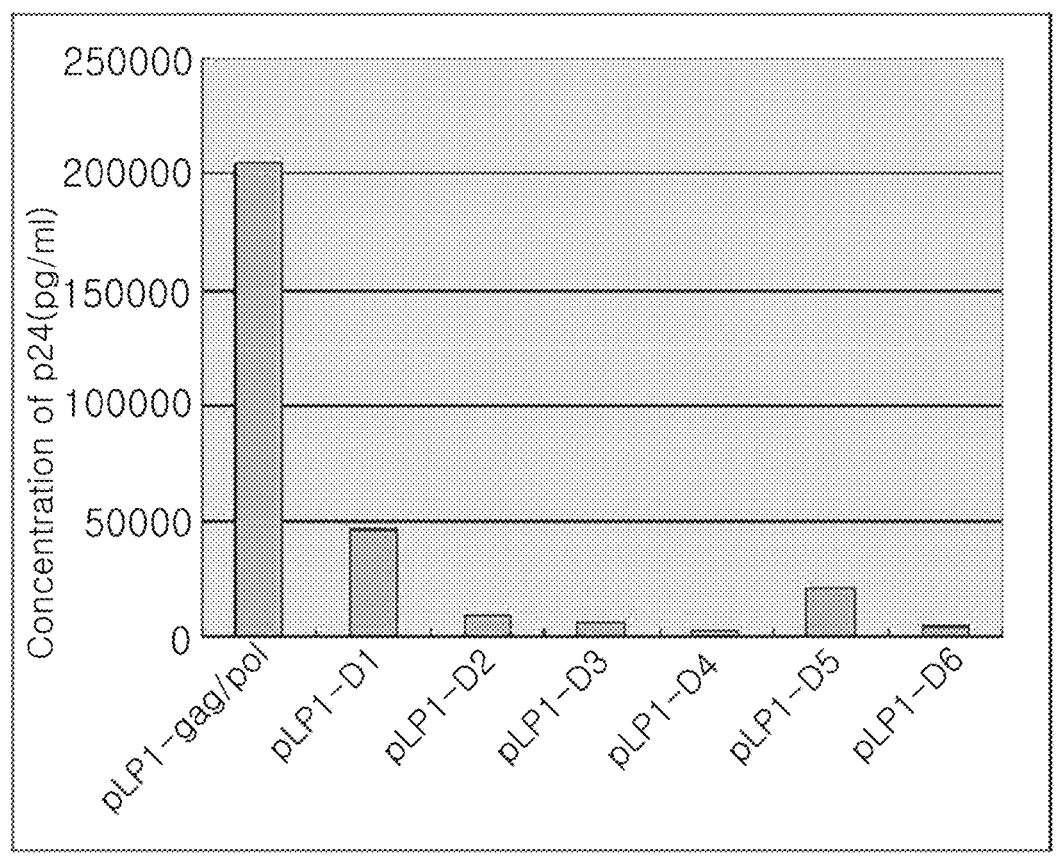
FIG. 5 shows the effects of inhibiting proliferation of HIV in the 6 gag deleted mutants which contain HIV NC protein, respectively.

As a result, as can be seen in FIG. 5 and Table 3 (unit: pg/ml) below, the six kinds of NC protein-containing Gag deletion mutants all inhibited the production of the HIV virus. Such results suggest that not only the NC protein itself, but also a peptide containing the NC protein, have the effect of inhibiting the proliferation of HIV virus.

TABLE 3

|  | 24 hr |
|---|---|
| pNL4-3EGFP(1 μg) + pLP1-gag/pol(1 μg) | 204652.942 |
| pNL4-3EGFP(1 μg) + pLP1-D1(1 μg) | 46076.011 |
| pNL4-3EGFP(1 μg) + pLP1-D2(1 μg) | 8973.306 |
| pNL4-3EGFP(1 μg) + pLP1-D3(1 μg) | 6346.566 |
| pNL4-3EGFP(1 μg) + pLP1-D4(1 μg) | 3063.140 |
| pNL4-3EGFP(1 μg) + pLP1-D5(1 μg) | 20383.209 |
| pNL4-3EGFP(1 μg) + pLP1-D6(1 μg) | 4540.682 |

INDUSTRIAL APPLICABILITY

As described in the above, the polypeptide comprising HIV NC protein, when it is overexpressed, has the effect on inhibiting HIV proliferation. Accordingly, the present invention provides not only the means of inhibition of HIV proliferation, but also the novel method for preventing and treating AIDS.

The invention claimed is:

1. A method for inhibiting Human Immunodeficiency Virus (HIV) proliferation comprising the steps of:
   (a) providing an expression vector comprising a promoter and a polynucleotide encoding a polypeptide consisting of wild-type HIV nucleocapsid (NC) protein operably linked to the promoter;
   (b) transfecting an HIV infected cell with the expression vector of step (a); and
   (c) expressing the polypeptide comprising the wild-type HIV nucleocapsid (NC) protein in the cell, wherein the expression inhibits HIV proliferation.

2. The method for inhibiting HIV proliferation comprising the step of transferring a polypeptide consisting of a wild-type HIV NC protein to an HIV infected target cell, wherein the transfer of the polypeptide increases the intracellular level of a polypeptide comprising wild-type HIV NC protein.

3. The method of claim 1, wherein the expression vector is pLP1/optiNC vector.

4. The method of claim 1 wherein HIV proliferation is inhibited by about 100-fold.

* * * * *

SEQUENCE LISTING

```
<160> NUMBER OF SEQ ID NOS: 21

<210> SEQ ID NO 1
<211> LENGTH: 55
<212> TYPE: PRT
<213> ORGANISM: Artificial Sequence
<220> FEATURE:
<223> OTHER INFORMATION: HIV opti-NC

<400> SEQUENCE: 1

Met Gln Arg Gly Asn Phe Arg Asn Gln Arg Lys Thr Val Lys Cys Phe
  1               5                  10                  15

Asn Cys Gly Lys Glu Gly His Ile Ala Lys Asn Cys Arg Ala Pro Arg
             20                  25                  30

Lys Lys Gly Cys Trp Arg Cys Gly Arg Glu Gly His Gln Met Lys Asp
         35                  40                  45

Cys Thr Glu Arg Gln Ala Asn
     50                  55

<210> SEQ ID NO 2
<211> LENGTH: 367
<212> TYPE: PRT
<213> ORGANISM: Artificial Sequence
<220> FEATURE:
<223> OTHER INFORMATION: gag mutant comprising HIV NC protein - D1

<400> SEQUENCE: 2
```

Met Val Gln Asn Ile Gln Gly Gln Met Val His Gln Ala Ile Ser Pro
1               5                   10                  15

Arg Thr Leu Asn Ala Trp Val Lys Val Val Glu Glu Lys Ala Phe Ser
            20                  25                  30

Pro Glu Val Ile Pro Met Phe Ser Ala Leu Ser Glu Gly Ala Thr Pro
        35                  40                  45

Gln Asp Leu Asn Thr Met Leu Asn Thr Val Gly Gly His Gln Ala Ala
    50                  55                  60

Met Gln Met Leu Lys Glu Thr Ile Asn Glu Glu Ala Ala Glu Trp Asp
65                  70                  75                  80

Arg Val His Pro Val His Ala Gly Pro Ile Ala Pro Gly Gln Met Arg
                85                  90                  95

Glu Pro Arg Gly Ser Asp Ile Ala Gly Thr Thr Ser Thr Leu Gln Glu
            100                 105                 110

Gln Ile Gly Trp Met Thr His Asn Pro Pro Ile Pro Val Gly Glu Ile
        115                 120                 125

Tyr Lys Arg Trp Ile Ile Leu Gly Leu Asn Lys Ile Val Arg Met Tyr
    130                 135                 140

Ser Pro Thr Ser Ile Leu Asp Ile Arg Gln Gly Pro Lys Glu Pro Phe
145                 150                 155                 160

Arg Asp Tyr Val Asp Arg Phe Tyr Lys Thr Leu Arg Ala Glu Gln Ala
                165                 170                 175

Ser Gln Glu Val Lys Asn Trp Met Thr Glu Thr Leu Leu Val Gln Asn
            180                 185                 190

Ala Asn Pro Asp Cys Lys Thr Ile Leu Lys Ala Leu Gly Pro Gly Ala
        195                 200                 205

Thr Leu Glu Glu Met Met Thr Ala Cys Gln Gly Val Gly Gly Pro Gly
    210                 215                 220

His Lys Ala Arg Val Leu Ala Glu Ala Met Ser Gln Val Thr Asn Pro
225                 230                 235                 240

Ala Thr Ile Met Ile Gln Lys Gly Asn Phe Arg Asn Gln Arg Lys Thr
                245                 250                 255

Val Lys Cys Phe Asn Cys Gly Lys Glu Gly His Ile Ala Lys Asn Cys
            260                 265                 270

Arg Ala Pro Arg Lys Lys Gly Cys Trp Lys Cys Gly Lys Glu Gly His
        275                 280                 285

Gln Met Lys Asp Cys Thr Glu Arg Gln Ala Asn Phe Leu Gly Lys Ile
    290                 295                 300

Trp Pro Ser His Lys Gly Arg Pro Gly Asn Phe Leu Gln Ser Arg Pro
305                 310                 315                 320

Glu Pro Thr Ala Pro Pro Glu Glu Ser Phe Arg Phe Gly Glu Glu Thr
                325                 330                 335

Thr Thr Pro Ser Gln Lys Gln Glu Pro Ile Asp Lys Glu Leu Tyr Pro
            340                 345                 350

Leu Ala Ser Leu Arg Ser Leu Phe Gly Ser Asp Pro Ser Ser Gln
        355                 360                 365

<210> SEQ ID NO 3
<211> LENGTH: 138
<212> TYPE: PRT
<213> ORGANISM: Artificial Sequence
<220> FEATURE:
<223> OTHER INFORMATION: gag mutant comprising HIV NC protein - D2

<400> SEQUENCE: 3

```
Met Ala Glu Ala Met Ser Gln Val Thr Asn Pro Ala Thr Ile Met Ile
 1               5                  10                  15

Gln Lys Gly Asn Phe Arg Asn Gln Arg Lys Thr Val Lys Cys Phe Asn
             20                  25                  30

Cys Gly Lys Glu Gly His Ile Ala Lys Asn Cys Arg Ala Pro Arg Lys
         35                  40                  45

Lys Gly Cys Trp Lys Cys Gly Lys Glu Gly His Gln Met Lys Asp Cys
     50                  55                  60

Thr Glu Arg Gln Ala Asn Phe Leu Gly Lys Ile Trp Pro Ser His Lys
 65                  70                  75                  80

Gly Arg Pro Gly Asn Phe Leu Gln Ser Arg Pro Glu Pro Thr Ala Pro
                 85                  90                  95

Pro Glu Glu Ser Phe Arg Phe Gly Glu Glu Thr Thr Thr Pro Ser Gln
                100                 105                 110

Lys Gln Glu Pro Ile Asp Lys Glu Leu Tyr Pro Leu Ala Ser Leu Arg
            115                 120                 125

Ser Leu Phe Gly Ser Asp Pro Ser Ser Gln
        130                 135
```

<210> SEQ ID NO 4
<211> LENGTH: 124
<212> TYPE: PRT
<213> ORGANISM: Artificial Sequence
<220> FEATURE:
<223> OTHER INFORMATION: gag mutant comprising HIV NC protein - D3

<400> SEQUENCE: 4

```
Met Ile Gln Lys Gly Asn Phe Arg Asn Gln Arg Lys Thr Val Lys Cys
 1               5                  10                  15

Phe Asn Cys Gly Lys Glu Gly His Ile Ala Lys Asn Cys Arg Ala Pro
             20                  25                  30

Arg Lys Lys Gly Cys Trp Lys Cys Gly Lys Glu Gly His Gln Met Lys
         35                  40                  45

Asp Cys Thr Glu Arg Gln Ala Asn Phe Leu Gly Lys Ile Trp Pro Ser
     50                  55                  60

His Lys Gly Arg Pro Gly Asn Phe Leu Gln Ser Arg Pro Glu Pro Thr
 65                  70                  75                  80

Ala Pro Pro Glu Glu Ser Phe Arg Phe Gly Glu Glu Thr Thr Thr Pro
                 85                  90                  95

Ser Gln Lys Gln Glu Pro Ile Asp Lys Glu Leu Tyr Pro Leu Ala Ser
                100                 105                 110

Leu Arg Ser Leu Phe Gly Ser Asp Pro Ser Ser Gln
            115                 120
```

<210> SEQ ID NO 5
<211> LENGTH: 86
<212> TYPE: PRT
<213> ORGANISM: Artificial Sequence
<220> FEATURE:
<223> OTHER INFORMATION: gag mutant comprising HIV NC protein - D4

<400> SEQUENCE: 5

```
Met Ala Glu Ala Met Ser Gln Val Thr Asn Pro Ala Thr Ile Met Ile
 1               5                  10                  15

Gln Lys Gly Asn Phe Arg Asn Gln Arg Lys Thr Val Lys Cys Phe Asn
             20                  25                  30

Cys Gly Lys Glu Gly His Ile Ala Lys Asn Cys Arg Ala Pro Arg Lys
```

35                  40                  45

Lys Gly Cys Trp Lys Cys Gly Lys Glu Gly His Gln Met Lys Asp Cys
             50                  55                  60

Thr Glu Arg Gln Ala Asn Phe Leu Gly Lys Ile Trp Pro Ser His Lys
 65                  70                  75                  80

Gly Arg Pro Gly Asn Phe
                85

<210> SEQ ID NO 6
<211> LENGTH: 70
<212> TYPE: PRT
<213> ORGANISM: Artificial Sequence
<220> FEATURE:
<223> OTHER INFORMATION: gag mutant comprising HIV NC protein - D5

<400> SEQUENCE: 6

Met Ala Glu Ala Met Ser Gln Val Thr Asn Pro Ala Thr Ile Met Ile
 1               5                  10                  15

Gln Lys Gly Asn Phe Arg Asn Gln Arg Lys Thr Val Lys Cys Phe Asn
                20                  25                  30

Cys Gly Lys Glu Gly His Ile Ala Lys Asn Cys Arg Ala Pro Arg Lys
            35                  40                  45

Lys Gly Cys Trp Lys Cys Gly Lys Glu Gly His Gln Met Lys Asp Cys
         50                  55                  60

Thr Glu Arg Gln Ala Asn
 65                  70

<210> SEQ ID NO 7
<211> LENGTH: 72
<212> TYPE: PRT
<213> ORGANISM: Artificial Sequence
<220> FEATURE:
<223> OTHER INFORMATION: gag mutant comprising HIV NC protein - D6

<400> SEQUENCE: 7

Met Ile Gln Lys Gly Asn Phe Arg Asn Gln Arg Lys Thr Val Lys Cys
 1               5                  10                  15

Phe Asn Cys Gly Lys Glu Gly His Ile Ala Lys Asn Cys Arg Ala Pro
                20                  25                  30

Arg Lys Lys Gly Cys Trp Lys Cys Gly Lys Glu Gly His Gln Met Lys
            35                  40                  45

Asp Cys Thr Glu Arg Gln Ala Asn Phe Leu Gly Lys Ile Trp Pro Ser
         50                  55                  60

His Lys Gly Arg Pro Gly Asn Phe
 65                  70

<210> SEQ ID NO 8
<211> LENGTH: 165
<212> TYPE: DNA
<213> ORGANISM: Artificial Sequence
<220> FEATURE:
<223> OTHER INFORMATION: HIV opti-NC

<400> SEQUENCE: 8
atgcagcggg gaaacttcag gaaccagcga aaaactgtga agtgcttcaa ttgcggaaag     60
gagggccaca tcgctaagaa ctgccgggcc cccagaaaga aaggctgctg gagatgcggc    120
agagagggcc accagatgaa ggactgcact gagcggcagg caaac                    165

<210> SEQ ID NO 9

<211> LENGTH: 1101
<212> TYPE: DNA
<213> ORGANISM: Artificial Sequence
<220> FEATURE:
<223> OTHER INFORMATION: gag mutant comprising HIV NC protein - D1

<400> SEQUENCE: 9

| gtgcagaaca tccaggggca atggtacat caggccatat cacctagaac tttaaatgca | 60 |
| tgggtaaaag tagtagaaga aaggctttc agcccagaag tgatacccat gttttcagca | 120 |
| ttatcagaag gagccacccc acaagattta aacaccatgc taaacacagt gggggacat | 180 |
| caagcagcca tgcaaatgtt aaaagagacc atcaatgagg aagctgcaga atgggataga | 240 |
| gtgcatccag tgcatgcagg gcctattgca ccaggccaga tgagagaacc aaggggaagt | 300 |
| gacatagcag gaactactag tacccttcag gaacaaatag gatggatgac acataatcca | 360 |
| cctatcccag taggagaaat ctataaaaga tggataatcc tgggattaaa taaaatagta | 420 |
| agaatgtata gccctaccag cattctggac ataagacaag gaccaaagga acccttaga | 480 |
| gactatgtag accgattcta taaaactcta agagccgagc aagcttcaca agaggtaaaa | 540 |
| aattggatga cagaaacctt gttggtccaa aatgcgaacc cagattgtaa gactatttta | 600 |
| aaagcattgg gaccaggagc gacactagaa gaaatgatga cagcatgtca gggagtgggg | 660 |
| ggacccggcc ataaagcaag agttttggct gaagcaatga gccaagtaac aaatccagct | 720 |
| accataatga tacagaaagg caattttagg aaccaaagaa agactgttaa gtgttttcaat | 780 |
| tgtggcaaag aagggcacat agccaaaaat tgcagggccc ctaggaaaaa gggctgttgg | 840 |
| aaatgtggaa aggaaggaca ccaaatgaaa gattgtactg agagacaggc taattttta | 900 |
| gggaagatct ggccttccca agggaagg ccagggaatt tccttcagag cagaccagag | 960 |
| ccaacagccc caccagaaga gagcttcagg tttggggaag agacaacaac tccctctcag | 1020 |
| aagcaggagc cgatagacaa ggaactgtat cctttagctt ccctcagatc actctttggc | 1080 |
| agcgacccct cgtcacaata a | 1101 |

<210> SEQ ID NO 10
<211> LENGTH: 414
<212> TYPE: DNA
<213> ORGANISM: Artificial Sequence
<220> FEATURE:
<223> OTHER INFORMATION: gag mutant comprising HIV NC protein - D2

<400> SEQUENCE: 10

| gctgaagcaa tgagccaagt aacaaatcca gctaccataa tgatacagaa aggcaatttt | 60 |
| aggaaccaaa gaaagactgt taagtgtttc aattgtggca agaagggca catagccaaa | 120 |
| aattgcaggg cccctaggaa aaagggctgt tggaaatgtg gaaaggaagg acaccaaatg | 180 |
| aaagattgta ctgagagaca ggctaatttt ttagggaaga tctggccttc ccacaaggga | 240 |
| aggccaggga atttcttca gagcagacca gagccaacag ccccaccaga gagagcttc | 300 |
| aggtttgggg aagagacaac aactccctct cagaagcagg agccgataga caaggaactg | 360 |
| tatcctttag cttccctcag atcactcttt ggcagcgacc cctcgtcaca ataa | 414 |

<210> SEQ ID NO 11
<211> LENGTH: 372
<212> TYPE: DNA
<213> ORGANISM: Artificial Sequence
<220> FEATURE:
<223> OTHER INFORMATION: gag mutant comprising HIV NC protein - D3

<400> SEQUENCE: 11

```
atgatacaga aaggcaattt taggaaccaa agaaagactg ttaagtgttt caattgtggc    60
aaagaagggc acatagccaa aaattgcagg gcccctagga aaaagggctg ttggaaatgt   120
ggaaaggaag gacaccaaat gaaagattgt actgagagac aggctaattt tttagggaag   180
atctggcctt cccacaaggg aaggccaggg aattttcttc agagcagacc agagccaaca   240
gccccaccag aagagagctt caggtttggg aagagacaa caactccctc tcagaagcag   300
gagccgatag acaaggaact gtatccttta gcttccctca gatcactctt tggcagcgac   360
ccctcgtcac aa                                                       372
```

<210> SEQ ID NO 12
<211> LENGTH: 258
<212> TYPE: DNA
<213> ORGANISM: Artificial Sequence
<220> FEATURE:
<223> OTHER INFORMATION: gag mutant comprising HIV NC protein - D4

<400> SEQUENCE: 12

```
atggctgaag caatgagcca agtaacaaat ccagctacca taatgataca gaaaggcaat    60
tttaggaacc aaagaaagac tgttaagtgt ttcaattgtg gcaaagaagg gcacatagcc   120
aaaaattgca gggcccctag gaaaaagggc tgttggaaat gtggaaagga aggacaccaa   180
atgaaagatt gtactgagag acaggctaat ttttaggga gatctggcc ttcccacaag    240 ggaaggccag ggaatttt                                                 258
```

<210> SEQ ID NO 13
<211> LENGTH: 210
<212> TYPE: DNA
<213> ORGANISM: Artificial Sequence
<220> FEATURE:
<223> OTHER INFORMATION: gag mutant comprising HIV NC protein - D5

<400> SEQUENCE: 13

```
atggctgaag caatgagcca agtaacaaat ccagctacca taatgataca gaaaggcaat    60
tttaggaacc aaagaaagac tgttaagtgt ttcaattgtg gcaaagaagg gcacatagcc   120
aaaaattgca gggcccctag gaaaaagggc tgttggaaat gtggaaagga aggacaccaa   180
atgaaagatt gtactgagag acaggctaat                                    210
```

<210> SEQ ID NO 14
<211> LENGTH: 216
<212> TYPE: DNA
<213> ORGANISM: Artificial Sequence
<220> FEATURE:
<223> OTHER INFORMATION: gag mutant comprising HIV NC protein - D6

<400> SEQUENCE: 14

```
atgatacaga aaggcaattt taggaaccaa agaaagactg ttaagtgttt caattgtggc    60
aaagaagggc acatagccaa aaattgcagg gcccctagga aaaagggctg ttggaaatgt   120
ggaaaggaag gacaccaaat gaaagattgt actgagagac aggctaattt tttagggaag   180
atctggcctt cccacaaggg aaggccaggg aatttt                             216
```

<210> SEQ ID NO 15
<211> LENGTH: 193
<212> TYPE: DNA
<213> ORGANISM: Artificial Sequence
<220> FEATURE:
<223> OTHER INFORMATION: HIV NC protein

<400> SEQUENCE: 15
aagcttcccg ggaatgcagc ggggaaactt caggaaccag cgaaaaactg tgaagtgctt      60
caattgcgga aaggagggcc acatcgctaa gaactgccgg gccccagaa agaaaggctg      120 ctggagatgc ggcagagagg gccaccagat gaaggactgc actgagcggc aggcaaactg    180
actgcaggaa ttc                                                        193

<210> SEQ ID NO 16
<211> LENGTH: 32
<212> TYPE: DNA
<213> ORGANISM: Artificial Sequence
<220> FEATURE:
<223> OTHER INFORMATION: D1 forward

<400> SEQUENCE: 16
tttctagagg acacgtgatg gtgcagaaca tc                                    32

<210> SEQ ID NO 17
<211> LENGTH: 32
<212> TYPE: DNA
<213> ORGANISM: Artificial Sequence
<220> FEATURE:
<223> OTHER INFORMATION: D2, D4, D5 forward

<400> SEQUENCE: 17
tttctagagg acacgtgatg gctgaagcaa tg                                    32

<210> SEQ ID NO 18
<211> LENGTH: 29
<212> TYPE: DNA
<213> ORGANISM: Artificial Sequence
<220> FEATURE:
<223> OTHER INFORMATION: D3, D6 forward

<400> SEQUENCE: 18
tttgtagagg acacgtgatg atacagaaa                                        29

<210> SEQ ID NO 19
<211> LENGTH: 26
<212> TYPE: DNA
<213> ORGANISM: Artificial Sequence
<220> FEATURE:
<223> OTHER INFORMATION: D1, D2, D3 reverse

<400> SEQUENCE: 19
ccctcgagtc cggattattg tgacga                                           26

<210> SEQ ID NO 20
<211> LENGTH: 29
<212> TYPE: DNA
<213> ORGANISM: Artificial Sequence
<220> FEATURE:
<223> OTHER INFORMATION: D4, D6 reverse

<400> SEQUENCE: 20
ccctcgagtc cggatcaaaa attccctgg                                        29

<210> SEQ ID NO 21
<211> LENGTH: 29
<212> TYPE: DNA
<213> ORGANISM: Artificial Sequence
<220> FEATURE:
<223> OTHER INFORMATION: D5 reverse -continued

```
<400> SEQUENCE: 21
ccctcgagtc cggatcaatt agcctgtct                                29
```